United States Patent
Samuelson et al.

(10) Patent No.: US 7,332,297 B2
(45) Date of Patent: Feb. 19, 2008

(54) ENZYMATIC POLYMERIZATION

(75) Inventors: Lynne A. Samuelson, Marlborough, MA (US); Ferdinando Bruno, Andover, MA (US); Sukant K. Tripathy, deceased, late of Acton, MA (US); by Susan Tripathy, legal representative, Acton, MA (US); Ramaswamy Nagarajan, Lowell, MA (US); Jayant Kumar, Westford, MA (US); Wei Liu, Lowell, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 285 days.

(21) Appl. No.: 10/390,676

(22) Filed: Mar. 14, 2003

(65) Prior Publication Data

US 2003/0186397 A1    Oct. 2, 2003

Related U.S. Application Data (62) Division of application No. 09/334,105, filed on Jun. 16, 1999, now Pat. No. 6,569,651.

(51) Int. Cl.
- *C12P 1/00* (2006.01)
- *C12P 13/00* (2006.01)
- *C12P 7/00* (2006.01)
- *C12N 11/16* (2006.01)
- *C12N 11/08* (2006.01)
- *C08G 73/00* (2006.01)

(52) U.S. Cl. ............ 435/41; 435/128; 435/132; 435/155; 435/174; 435/180; 435/817; 424/400; 528/422

(58) Field of Classification Search ............. None
See application file for complete search history.

(56) References Cited

U.S. PATENT DOCUMENTS 3,730,841 A * 5/1973 Salvatore et al. .......... 435/182
6,018,018 A * 1/2000 Samuelson et al. ........ 528/422
7,001,996 B1 * 2/2006 Samuelson et al. ....... 536/23.1

OTHER PUBLICATIONS

Liu et al., J. Am. Chem. Soc., vol. 121, Dec. 19, 1998, pp. 71-78.*
Liu et al., Mat. Res. Soc. Symp. Proc., vol. 247, 1992, pp. 601-606.*
Samuelson et al., Macromolecules, vol. 31, No. 13, Jun. 5, 1998, pp. 4376-4378.*
Xu et al., Materials Science and Engiineering, C4, 1996, pp. 161-168.*
Akkara et al., Biomimetics, vol. 2, No. 4, 1994, pp. 331-339.*

* cited by examiner

Primary Examiner—David M. Naff
(74) Attorney, Agent, or Firm—Vincent J. Ranucci (57) ABSTRACT

The invention relates to a novel method for enzymatic polymerization which includes (1) obtaining a reaction mixture including a monomer, a template, and an enzyme; and (2) incubating the reaction mixture for a time and under conditions sufficient for the monomer to align along the template and polymerize to form a polymer-template complex. The template can be a micelle, a borate-containing electrolyte, or lignin sulfonate. Such a complex possesses exceptional electrical and optical stability, water solubility, and processibility, and can be used in applications such as light-weight energy storage devices (e.g., rechargeable batteries), electrolytic capacitors, anti-static and anti-corrosive coatings for smart windows, and biological sensors.

1 Claim, 9 Drawing Sheets

ENZYMATIC POLYMERIZATION

RELATED APPLICATION

This is a division of application Ser. No. 09/334,105, filed Jun. 16, 1999, now U.S. Pat. No. 6,569,651.

This invention was made with Government support under ARO Cooperative Grant DAAH04-94-2-003. The Government may have certain rights in the invention.

FIELD OF THE INVENTION

The invention relates to methods for polymerizing a monomer enzymatically in the presence of a template to form a polymer-template complex.

BACKGROUND OF THE INVENTION

Recently, there has been an increased interest in the tailored development of certain classes of polymers, such as electrically conductive and optically active polymers (e.g. polythiophene, polypyrrole, and polyaniline) for application to wider ranges of use. Examples of such uses include light-weight energy storage devices, electrolytic capacitors, anti-static and anti-corrosive coatings for smart windows, and biological sensors. However, the potential applications of these polymers have been limited by some fundamental properties of the monomers employed to form these polymers and by limitations of known polymerization techniques.

Electrically conductive and optically active polymers are relatively insoluble in water. Therefore, these polymers are typically formed in an organic solvent. Attempts to increase the water solubility of these polymers have included derivatization of the monomer before polymerization or the resulting polymer formed. However, derivatization of monomers typically slows polymerization, while derivatization of polymers generally causes some degradation.

Moreover, the physical properties of polymeric materials generally can be manipulated only by mechanical means such as extrusion, or by polarization of relatively short polymers or oligomers in an electric field. Further, the existing synthetic methods of forming polymers generally do not provide means for manipulating their shape during polymerization.

Therefore, a need exists to overcome or minimize the above-referenced problems associated with polymer synthesis.

SUMMARY OF THE INVENTION

The invention relates to novel methods for enzymatic polymerization which include (1) obtaining a reaction mixture including a monomer, a template, and an enzyme, and (2) polymerizing the monomer aligning along the template to form a polymer-template complex. Not only does such a complex possess high molecular weight, high water solubility, and exceptional electrical and optical properties, its preparation is also simple, environmentally friendly, and inexpensive. Its excellent properties enable the complex to be used in many applications. For example, polyaniline-lignin sulfonate complexes can be used as an emulsifier in asphalt, or a dispersant for cement mixes, fertilizers, linoleum paste, dust suppressants, dyes and pigments. As another example, new polyaniline-micelle complexes, which form a spherical polymer shell, can be used for paints, coatings, and also for entrapping and transporting materials, e.g., pharmaceuticals, that are generally insoluble in aqueous media.

One aspect of this invention relates to novel methods for enzymatic polymerization. The methods include obtaining a reaction mixture including a monomer (e.g., aniline or phenol), a micelle (e.g., a micelle template with positively charged or negatively charged groups on the surface), and an enzyme (e.g., a peroxidase such as horseradish peroxidase); and incubating the reaction mixture for a time and under conditions sufficient for the monomer to align around the micelle surface and polymerize to form a polymer-micelle complex. The method further includes combining an electron acceptor, such as hydrogen peroxide, with the reaction mixture to initiate the polymerization. The reaction mixture in the novel method has a pH of between about 4 and about 10 (e.g., between about 6 and about 8).

The micelles used in the novel methods include multiple units. Each unit has a hydrophobic part and a hydrophilic part. The hydrophilic part includes an aromatic ring (e.g., benzene) bonded to an acidic substituent (e.g., sulfonate) with a $pK_a$ of the acidic substituent ranging from 0.5 to 3.5 (e.g., 0.5 to 2.5). Some examples of such a micelle unit are dodecyl benzene sulfonic acid, octadecyl benzene sulfonic acid, and hexadecyl naphthyl sulfonic acid.

Another aspect of this invention relates to novel polymer-micelle complexes including a polymer bound to a micelle. The novel complexes have a molecular weight ranging from 70 kD to 10,000 kD (e.g., 100 kD to 7,000 kD) and can be electrically conducting and/or water soluble. The novel complexes can also be optically active. An example of the novel complex is polymer-dodecyl benzene sulfonic acid (e.g., polyaniline-dodecyl benzene sulfonic acid or polyphenol-dodecyl benzene sulfonic acid).

A further aspect of this invention relates to a novel method for enzymatic polymerization. The method includes obtaining a reaction mixture including a monomer (e.g., aniline or phenol), a template, and an enzyme (e.g., a peroxidase such as horseradish peroxidase); and incubating the reaction mixture for a time and under conditions sufficient for the monomer to align along the template and polymerize to form a polymer-template complex. The method further includes combining hydrogen peroxide with the reaction mixture to initiate the polymerization. The reaction mixture in the novel method has a pH that is greater than 4 (e.g., between about 4 and about 10 or between about 6 and about 8).

The template can be lignin sulfonate or a borate-containing polyelectrolyte; both of which contain charged groups (i.e., sulfonate or borate) that are responsible, at least in part, for aligning the charged monomers. Borate-containing polyelectrolytes can be a polymer (e.g., polyvinyl) containing positively or negatively charged groups. Examples of such charged groups include trifluoroborate [—$BF_3$]$^-$, trimethylborate [—$B(CH_3)_3$]$^-$, and hydrobis(pyridine)boron [—BH$(C_5H_5N)_2$]$^+$.

A still further aspect of this invention relates to novel polymer-template complexes including a polymer bound to a template. The novel complexes have a molecular weight ranging from 70 kD to 10,000 kD (e.g., 100 kD to 7,000 kD). The complexes can be electrically conducting and/or water soluble and can act as a charge-transfer complex or an optically active complex. Examples of the novel complexes include polymer-lignin sulfonate (e.g., polyaniline-lignin sulfonate or polyphenol-lignin sulfonate) and polymer-borate-containing polyelec-trolyte (e.g., polyaniline-tetrafluoroborate-containing polyelectrolyte or polyphenol-tetramethylborate-containing polyelectrolyte).

A template binds to and aligns the monomers so as to maximize conjugation and minimize branching of the polymers formed according to the new methods. The template can be a polyelectrolyte. The template can also be a micelle, an oligomer, or a polymer. Examples of suitable templates include an azo polymer, a substituted polystyrene, a substituted vinyl polymer (e.g., polyvinyl phosphonate, polyvinyl phosphate, or polyvinyl benzoic acid), a sulfonated polymer (e.g., lignin sulfonate, sulfonated polystyrene, or polystyrene sulfonic acid), a polynucleotide (e.g., deoxyribonucleotide or ribonucleotide), a polypeptide, a protein, a biological receptor, a zeolite, a caged compound, an azopolymer, an vinyl polymers (e.g., polyvinyl benzoic acid, polyvinyl phosphate, or polyvinyl borate), polyphenol red, azo compounds, a dendrimer, a protein, or sulfonated micelles (e.g., micelle containing dodecyl benzene sulfonic acid). The template can be positively charged, such as a polycation (e.g., poly(diallyl dimethyl ammonium chloride)) or negatively charged, such as a polyanion (e.g., sulfonated polystyrene). It is important that the charged groups of a template are indeed in their charged form under the required reaction conditions. For example, in the case of a polyanionic template (e.g., lignin sulfonate), the $pK_a$ value of the anionic functionalities (e.g., sulfonate) should be sufficiently low (e.g., from about 0.5 to about 3.5) to ensure that they are negatively charged under the reaction conditions (e.g., pH 4.0 to 10.0) so as to bind to and align the positively charged aniline monomers.

A conducting polymer refers to a polymer which exhibits conductivity ranging from about $10^{-10}$ to $10^6$ S/cm.

The new template-assisted enzymatic polymerization reactions address problems associated with existing methods of preparing electrically conductive polymers such as the need for harsh chemicals, high costs, difficulty in producing polymeric products with high water solubility and electrical conductivity, and the inability to control shapes and sizes of such products. The polymer-template complexes prepared by this novel polymerization, in addition to being electrically conductive and completely soluble in aqueous media, are also of high molecular weights (e.g., >70 kD).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict in terminology, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based on the discovery that a template, e.g., polymer or micelle, can effectively associate with a monomer and assist in enzymatic polymerization of such a monomer to produce a high molecular weight polymer complex. The novel enzymatic polymerization method produces polymers that display exceptional electrical and optical stability, water solubility, and processibility, while simultaneously providing a simple (one-step), environmentally friendly, and commercially attractive synthetic approach.

The new methods involve oxidizing a monomer by an enzyme such as peroxidase (e.g., agarose peroxidase, manganese peroxidase, lignin peroxidase, lactoperoxidase, or soybean peroxidase) or laccase. When aniline or phenol is the monomer, oxidation produces a free radical regioselectively at the ortho or para positions of the benzene ring. The oxidized monomers then undergo a coupling reaction to form a polymer with each other. Peroxidase and laccase enzymes typically require electron acceptors such as hydrogen peroxide, oxygen, alkyl hydroperoxide, or percarboxylic acid. The free radical-forming enzymatic reaction (with phenol as the monomer) is illustrated in Scheme I below:

Scheme I

Figures 1, 2:
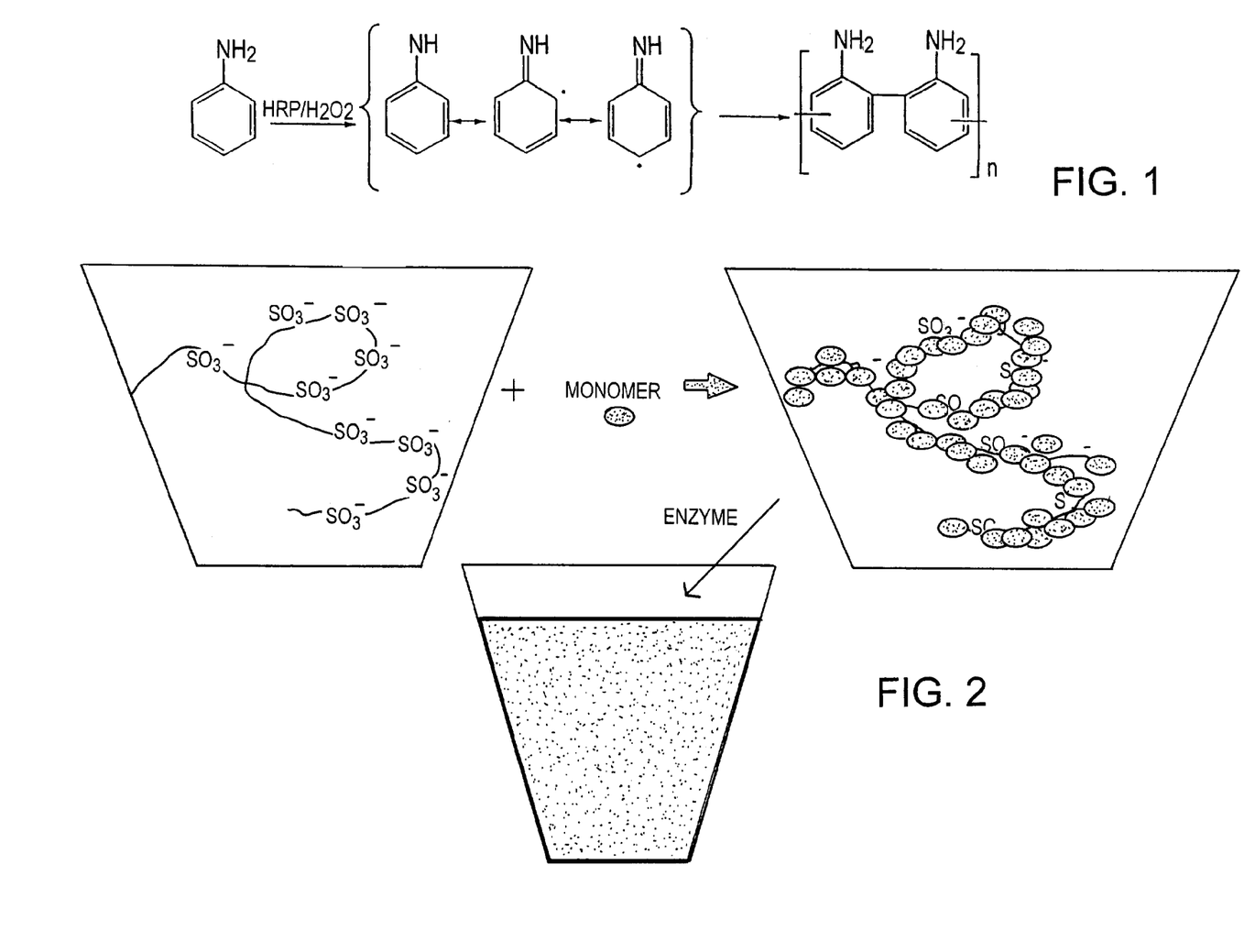
FIG. 1 is a scheme showing the general mechanism of enzymatic polymerization of aniline in the absence of a template.
FIG. 2 is a schematic representation of the novel template-assisted enzymatic polymerization. A monomer of interest is first added to an aqueous solution containing a polyelectrolyte template. Under the proper conditions, the monomer associates with the template. Upon adding a suitable enzyme (e.g., horseradish peroxidase) and an oxidant (e.g., hydrogen peroxide), the polymerization proceeds and results in a water-soluble polymer-template complex.

Although enzymatic polymerization in the absence of a template is environmentally friendly, and can offer a high degree of control over the kinetics of the reaction, it is not free of shortcomings. Apart from the fact that only low molecular weight products are obtained, such products are usually a mixture of both ortho- and para-substituted polymers. Further, these ortho- and para-substituted polymers are often branched, thus resulting in reduced electrical and optical properties. FIG. 1 is an illustration of how enzymatic polymerization (with aniline as a monomer) in the absence of a template can result in a complex with undesirable electrical properties such as reduced conductivity.

On the other hand, template-assisted enzymatic polymerization according to the invention minimizes branching of the product and promotes a para-directed, head-to-tail polymerization. A typical template-assisted polymerization reaction (with aniline as the monomer) is illustrated in Scheme II below.

In the case of polyaniline, the mechanism of polymerization is primarily para-directed and results in the electrically active form as shown in Scheme II above. This preferential alignment provides improved electrical and optical properties of the final polymer complex. Second, the template can serve as a large molecular dopant species that is complexed and essentially locked to the polymeric products, e.g., polyaniline or polyphenol. The use of these polymers in electronic and optical applications has been limited because of poor dopant stability. The small ionic dopants or chromophores that are used in existing methods diffuse away from the polymers with time and/or conditions. This locking of a large polyelectrolyte dopant to the polymer ensures that the electrical nature of the polymer's conjugated backbone structure is maintained and that the desired electrical and optical properties are stabilized. Third, the polyelectrolyte template provides water solubility of the final polymer-template complex for environmentally friendly, facile, and inexpensive processing.

The entire process of the novel enzymatic polymerization is illustrated by the drawing as shown in FIG. 2.

The solvent used in the novel polymerization method is typically water, but can include other organic solvents such as dimethyl formamide, methanol, ethanol, and dioxane. The pH of the solvent ranges from about 4.0 to about 10.0. Preferably, the pH is between about 4.0 and about 5.0 for aniline monomer and between about 6.0 and about 7.0 for phenol monomer. Examples of suitable buffers include Tris-HCl buffer, sodium phosphate, and HEPES.

The concentration of the enzyme in the novel polymerization reaction mixture should be adjusted to a level such that a significant increase in the reaction rate can be achieved. Typically, this concentration ranges from about

Scheme II

As shown in Scheme II, the template and the polymeric product form a stable complex. The template serves at least three critical functions. First, it serves as a charged scaffold upon which the monomers preferentially align themselves to form a complex, thereby promoting extended conjugation of the resulting polymer chains (limiting parasitic branching).

one unit/ml to about five units/ml, where one unit will form 1.0 mg purpurogallin from pyrogallol in 20 seconds at pH 6.0 at 20° C. Examples of suitable enzymes include peroxidases (e.g., horseradish peroxidase, agarose peroxidase, maganese peroxidase, lignin peroxidase, lactoperoxidase, or soybean peroxidase) and laccase.

Examples of suitable monomers include unsubstituted and substituted aniline (e.g., 2-methylaniline, 2-methoxy-5 methylaniline or 2-ethyl-5-methoxyaniline) as well as unsubstituted and substituted phenol (e.g., 2-ethylphenol, 3-methoxyphenol, or 2-ethoxy-5-isopropylphenol). The monomer can be a cation or an anion. Further, the monomer can be, for example, a dye, such as an azo compound, or a ligand. An oligomer can be employed rather than a monomer. Further, a mixture of different monomers, or even a mixture of oligomers and monomers, can also be used to form polymers using the new methods. Generally, the concentration of a monomer used in the new methods ranges from about 10 mM to about 100 mM.

The concentration of a template added should be sufficient to enable monomers to align along the template throughout the polymerization reaction. Typically, the ratio of the template concentration to the monomer concentration ranges from about 1:10 to about 10:1.

The polymerization reaction is a redox reaction and typically is initiated by adding a suitable oxidant, such as a hydrogen peroxide or a alkyl hydroperoxide solution. In one embodiment, the hydrogen peroxide has a concentration range from about 1 mM to about 5 mM in the reaction mixture. The concentration of hydrogen peroxide solution added to the reaction mixture can be about 30%. The reaction mixture containing monomers, template, and enzyme is stirred while slowly adding the hydrogen peroxide solution to initiate the polymerization reaction. Typically, the reaction mixture is maintained at a temperature ranges from about 10° C. to about 25° C. during polymerization. The resulting polymer can be, for example, a linear polymer, such as an extended linear polymer intertwined with the polyelectrolyte template. Alternatively, the polymer can be dendritic, or branched. It should be noted that the electrical properties of a polymer diminish as it adopts a branched conformation.

The new polymers are electrically conducting because of the electrostatic interaction between the charged groups of the template and the monomer, e.g., aniline. When aniline is used as the monomer, at a low local environmental pH, e.g., pH 4.0, most of the aniline monomers are positively charged ($pK_a$=4.6). To ensure the aniline monomers will bind to the template, the template must also be in its charged form. Templates containing benzene sulfonate groups are particularly suitable because the $pK_a$ of such groups are about 0.7 and thus, these groups are negatively charged under the reaction conditions. The benzene rings of the charged groups and the monomers can also interact with each other to further stabilize the complex.

In other embodiments, the polymer can be polyaniline complexed with a polyelectrolyte template, wherein the polyaniline is an extended linear polymer intertwined with the polyelectrolyte template. In a specific embodiment, the polyaniline is a component of a water soluble, electrically conducting complex. The temperature of the reaction mixture can be maintained at a temperature of about 20° C. during polymerization.

Optionally, the method of the invention includes forming a layer of the polymer on a surface. In this embodiment, the pH of the polymer solution is reduced to a suitable pH, such as a pH between about 2.0 and about 8.0, by adding a suitable acid, such as hydrochloric acid or acetic acid. A suitable surface, such as a glass slide treated with an alkali, such as Chemsolv® alkali, is immersed in a polymer solution for a sufficient period of time to cause the polymer to assemble onto the surface via electrostatic interaction. In one embodiment, a glass slide is immersed in a polymer solution for about ten minutes and then removed. The surface can then be washed with water at a pH of about 2.5 to remove unbound polymer from the surface.

Distinct layers of polymers can be applied to a surface by this method. For example, an initial layer can be formed by exposing a suitable surface to a polyanion formed by the methods of the invention, and then subsequently exposing the same surface, having the polyanion deposited upon it, into a solution of a polycation. In one specific embodiment, a glass slide treated with Chemsolv® alkali is exposed to a one mg/ml solution of poly(diallyl dimethyl ammonium chloride) at a pH of 2.5 as a polycation, and then exposed to a one mg/ml solution of sulfonated polystyrene/polyaniline formed by the method of the invention, as a polyanion. A bilayer of polymers is thereby formed. Additional layers of these or other polymers can subsequently be applied. By using this method, a film of polymer layers can be tailor-made to have certain functionalities and thickness. These polymer films can be used as protective coatings, antistatic coatings, or optical filters.

In another embodiment, where the template is an oligomer, polymerization of the template can be initiated simultaneously with, or subsequent to alignment and polymerization of the bound monomer or oligomer. In still another embodiment, the template can be removed from the resulting polymer, such as by decomposition or dissolution, to leave behind a polymer shell.

In one specific embodiment of the methods of the invention, the template-assisted enzymatic polymerization of aniline is carried out in an aqueous solution using 0.1 M sodium phosphate or tris-HCl buffer and a pH ranging from about 4.0 to about 10.0. Aniline monomers typically can be added in a range of between about 10 mM and about 100 mM, and an appropriate amount of a template, in this case sulfonated polystyrene (SPS; molecular weight of 70,000), is added in ratios ranging from about 1:10 to about 10:1 SPS/aniline. The enzyme horseradish peroxidase is then added to the reaction mixture in a range of about one unit/ml to about five units/ml. To initiate the reaction, an oxidizer such as hydrogen peroxide, is slowly added in 10 µl increments over a reaction time of 3 hours, with constant stirring to a final concentration ranging from about 10 mM to about 100 mM.

In another specific embodiment of the new methods, the template-assisted enzymatic polymerization of phenol is carried out in an aqueous solution using 0.1 M sodium phosphate or tris-HCl buffer at a pH ranging from about 4.0 to 10.0. Phenol monomers are added in a range from about 10 mM to about 100 mM, and an appropriate amount of the template SPS is added in ratios ranging from about 1:10 to about 10:1 SPS/phenol. Horseradish peroxidase is then added to the reaction mixture in a range of approximately one to five units/ml. To initiate the reaction, an oxidizer, such as hydrogen peroxide, is slowly added in 10 µl increments over a reaction time of about 3 hours, with constant stirring to a final concentration ranging from about 10 mM to about 100 mM.

Figure 3:
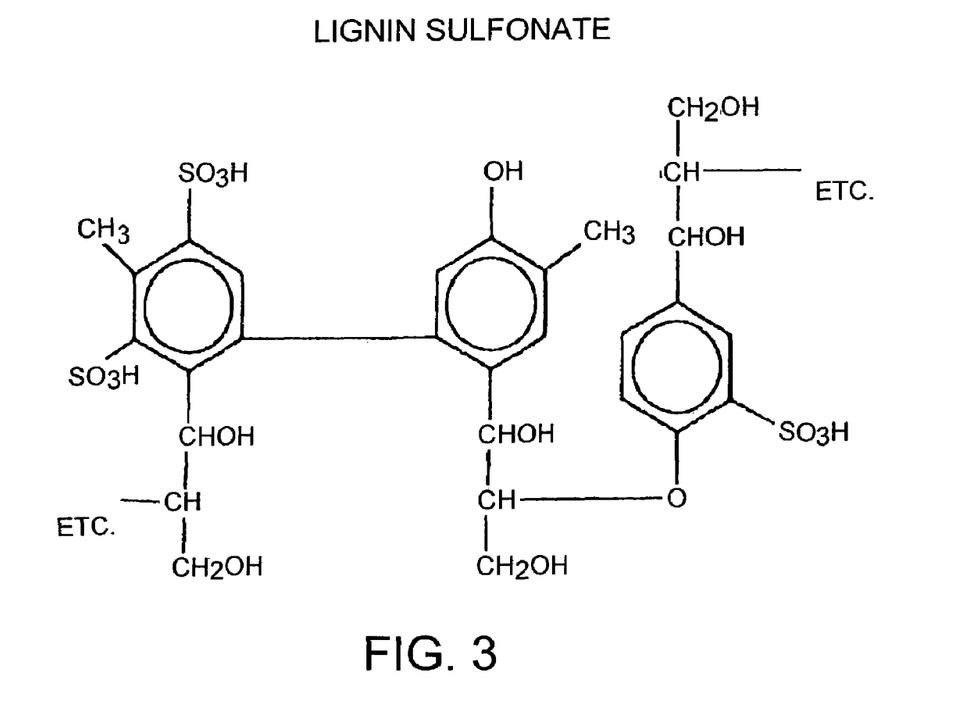
FIG. 3 is a generic chemical formula of a portion of lignin sulfonate.

In another embodiment, lignin sulfonate is used as a template in the novel polymerization reaction, thus resulting in an electrically conducting, water-soluble polymer which is doped by lignin sulfonate. See Example 3 below. Lignin is an abundant, non-toxic natural polymer that is becoming increasingly more important due to its versatility in performance. Lignin sulfonate is an inexpensive by-product from pulp processing industries, and has already been used in a wide variety of products based on its dispersing, binding, complexing, and emulsifying properties. Although the exact structure of lignin is not yet known, a generalized chemical formula of a known portion of lignin sulfonate is shown in FIG. 3.

In another embodiment, the template can be a micelle, thus resulting in an electrically conducting, water-soluble, high molecular weight polymer-micelle complex. Examples 4 and 5 below describe the preparation of polyaniline-dodecyl benzene sulfonic acid (DBSA) micelles and polyphenol-DBSA micelles, respectively. An important aspect of this embodiment is that micelles are spherically shaped with hydrophilic groups (i.e., charged head groups such as negatively charged benzene sulfonate) pointing out towards the aqueous-based solvent, and hydrophobic groups (i.e., tail groups such as dodecyl) pointing in towards the core of the micelle. Thus, monomers that align themselves upon the charged groups of the micelle template polymerize to form a spherical product.

The size (i.e., range of molecular weights) and uniformity of such spherical polymers can be easily controlled by adjusting the type of micelle template and the molar ratio of micelle to monomers. The molecular weight of the spherical polymeric products can reach as high as 10,000 kD. As mentioned above, it is critical for the head groups of a micelle template to be charged under the required reaction conditions for proper alignment of the monomers. Aside from DBSA, naphthalenesulfonic acid ($pK_a$=0.57) bonded to a hydrophobic tail group can also be used as a template in this embodiment. A generalized micelle-assisted polymerization reaction (with aniline as the monomer) is illustrated in Scheme III below. Note that only a portion of the micelle is shown.

Scheme III

-continued

= Dodecyl Benzene Sulfonic Acid

The novel polymer-micelle complexes can be used in a wide range of applications such as paints; coatings; emulsifiers in asphalt, pesticides, or pigments; sequestrants in water treatments; and dispersants for cement mixes, carbon black, and dust suppressants. The new methods also allow controlled entrapment of a variety of interesting molecular species such as various pharmaceuticals.

EXAMPLES

The invention is further described in the following examples, which do not limit the scope of the invention described in the claims.

Example 1

Preparation of Polyaniline-Sulfonated Polystyrene Complex

Horseradish peroxidase (HRP) (enzyme classification number (EC) 1.11.1.7), phosphate and Tris-HCl buffers were obtained from Sigma Chemicals Company, St. Louis, Mo. Aniline, sulfonated polystyrene ("SPS") and hydrogen peroxide (30%) were obtained from Aldrich Chemicals, Inc., Milwaukee, Wis. All the chemicals were used as received.

Figure 4:
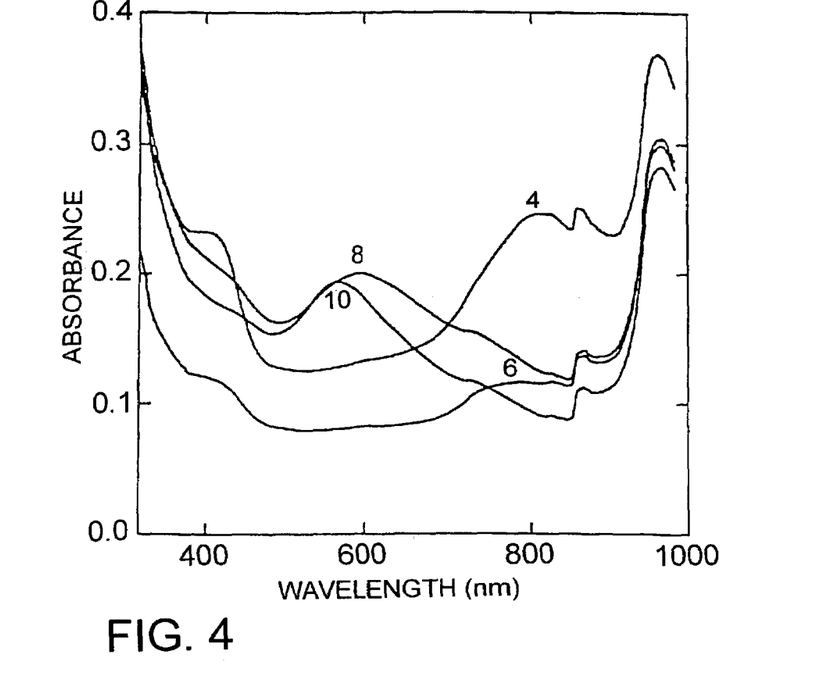
FIG. 4 is a graph of the visible absorption spectra of a polyaniline template complex (0.05 M aniline to 0.1 M sulfonated polystyrene (SPS)) formed at various pH values.

The progress of a template-assisted polymerization reaction of aniline in the presence of the template, SPS (in a 1:1 ratio) was monitored by the change in visible absorbance. A Perkin-Elmer Lambda-9® UV-Vis-near IR spectrophotometer was used for the spectral characterization of the polymer. FIG. 4 shows the visible absorption spectra of the sulfonated polystyrene/polyaniline (SPS/PA) complex prepared under various pH conditions of 4, 6, 8, and 10. As shown in FIG. 4, the SPS/PA complex, prepared at a pH of 4, exhibited a strong absorbance maximum at approximately 780 nm. This shows that the presence of an emeraldine form, i.e., an oxidized, electrically conducting form of polyaniline. Polymerization at higher pH resulted in an absorption maximum of about 600 nm, indicating a more insulating form of polyaniline. In all cases, the polymer complex did not precipitate out of solution, indicating that complexation of the polyaniline to the SPS had occurred.

Figure 5:
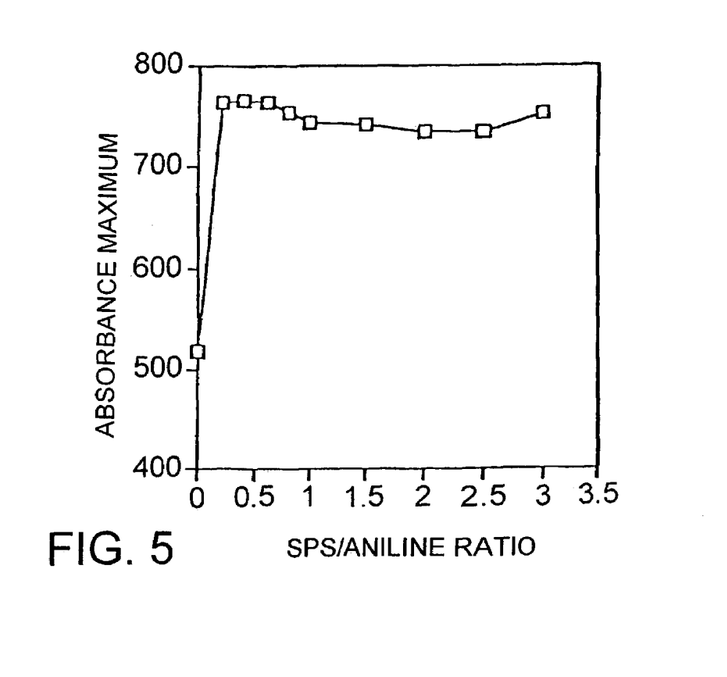
FIG. 5 is a graph of absorbance versus SPS/aniline ratio that can be used to find the optimum dopant-to-monomer ratio.

Next, the molar ratio of monomer to polyelectrolyte template (repeat unit) was optimized. FIG. 5 shows a plot of absorption maxima for various SPS/aniline ratios. As shown, a ratio of 1:2, SPS/aniline was the minimum ratio required to obtain the electrically conducting form of polyaniline, which had an absorption maximum at approximately 780 nm at a pH in a range of between about 4 and about 5.

Figure 6A:
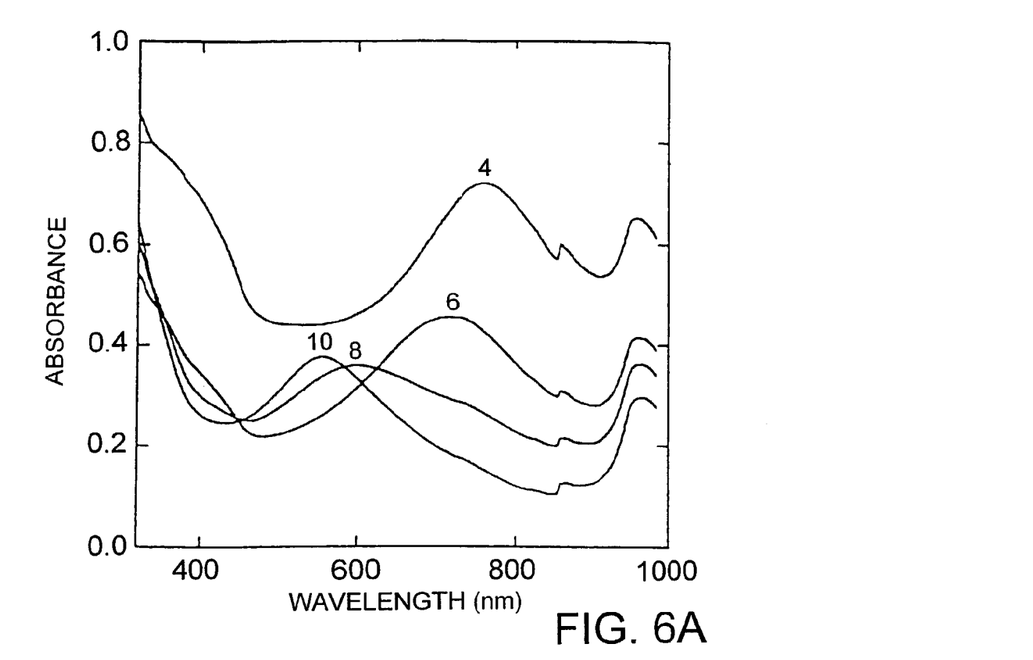
FIG. 6a is a graph showing the visible absorption and redox behavior of polyaniline/SPS prepared at pH 4.0 with increasing pH values.
Figure 6B:
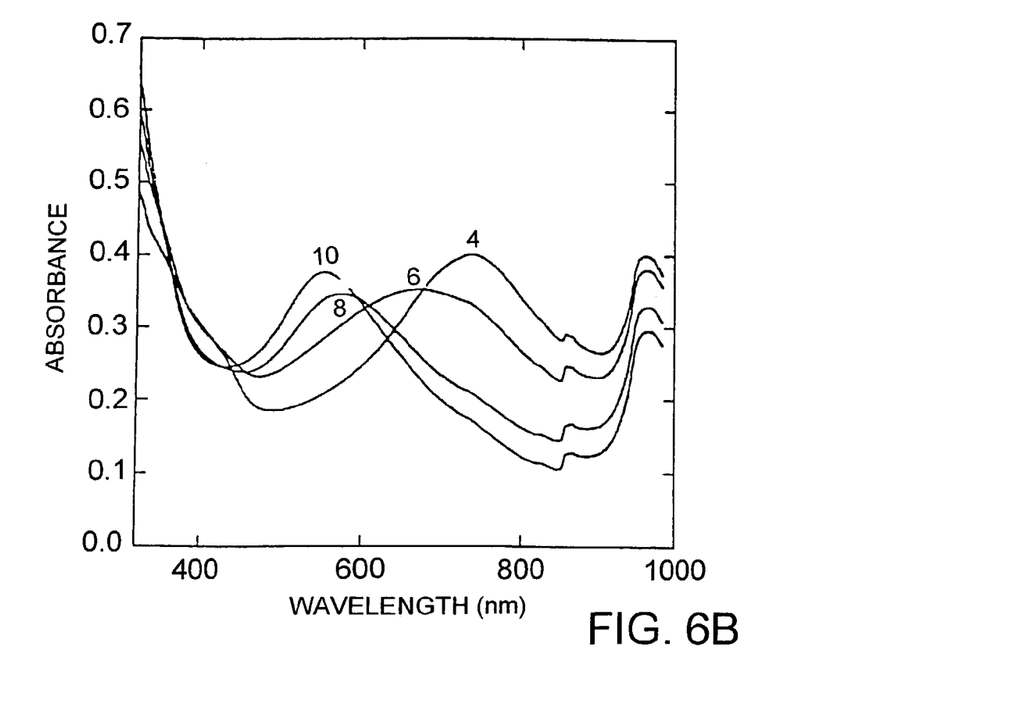
FIG. 6b is a graph showing the visible absorbance and redox behavior of polyaniline/SPS prepared at pH 4.0 with decreasing pH values.

The reversible reduction/oxidation (redox) behavior of the SPS/PA complex was monitored by measuring visible absorption of the complex's under various pH conditions. In all cases, the polymer complex was prepared at pH 4.0 to obtain the electrically active form of the polyaniline. The pH of the solution was then adjusted for the absorption maxima measurements. As shown in FIG. 6a, the SPS/PA complex shifted in absorption maxima to shorter wavelengths as the pH of the solution was increased. This indicated a reduction of the polyaniline backbone to a more insulating state. FIG. 6b shows the reverse behavior where the absorption maximum was found to shift back to longer wavelengths with decreasing pH conditions. This indicated oxidation of the polyaniline backbone back to a more electrically conductive state. This redox behavior was reversible and confirms that an electrically active form of polyaniline was present in the final SPS/PA template complex. Molecular weight was determined by column chromatography using Protein PAK 300 SW®-Waters Association columns. Molecular weight of approximately 74 kD was measured indicating polymerization of the aniline and complexation to the SPS template.

The SPS/PA complex was self-assembled onto glass slides by the layer-by-layer electrostatic deposition technique (Ferreira, M., et al., Thin Solid Films, 244:806 (1995) and Decher, G., et al., Thin Solid Films, 210-211 (1992)). A glass slide treated with alkali (Chemsolv® alkaline) was exposed to polycation and polyanion solutions repeatedly to transfer monolayers of these polyelectrolytes for every exposure. A one mg/ml solution of poly(diallyl dimethyl ammonium chloride) (PDAC) at pH 2.5 was used as the polycation, while approximately a one mg/ml solution of SPS/PA at pH 2.5 was used as the polyanion. The glass slide was exposed to each polyelectrolyte solution for 10 minutes and washed with water at the same pH (2.5) to remove the unbound polymer from the surface. This process was repeated to obtain the desired number of layers.

Figure 7A:
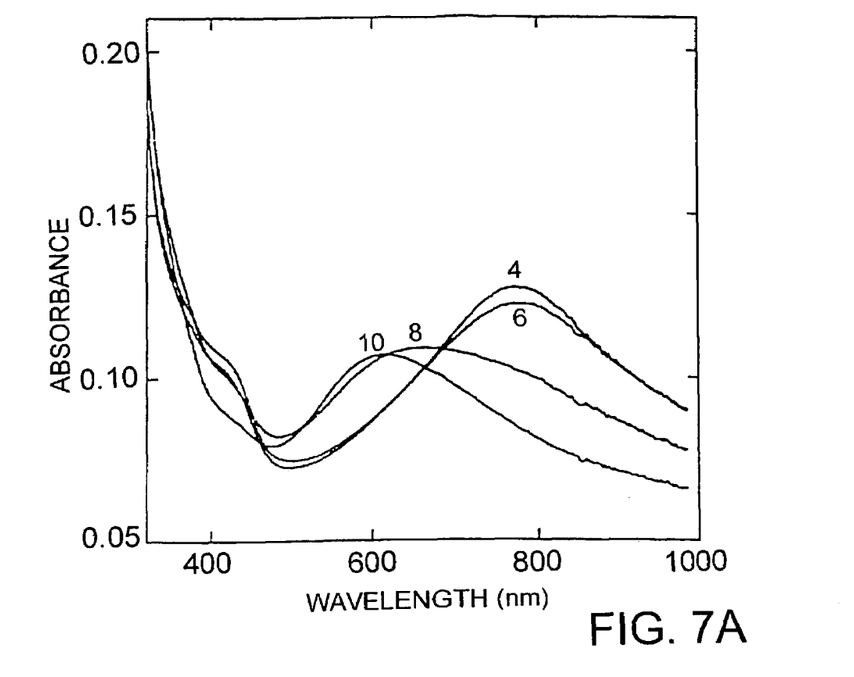
FIG. 7a is a graph showing the visible absorbance and redox behavior of a 50 bilayer film of poly(diallyl dimethyl ammonium chloride) (PDAC) alternating with SPS/polyaniline (prepared at pH 4.0) with increasing pH values.
Figure 7B:
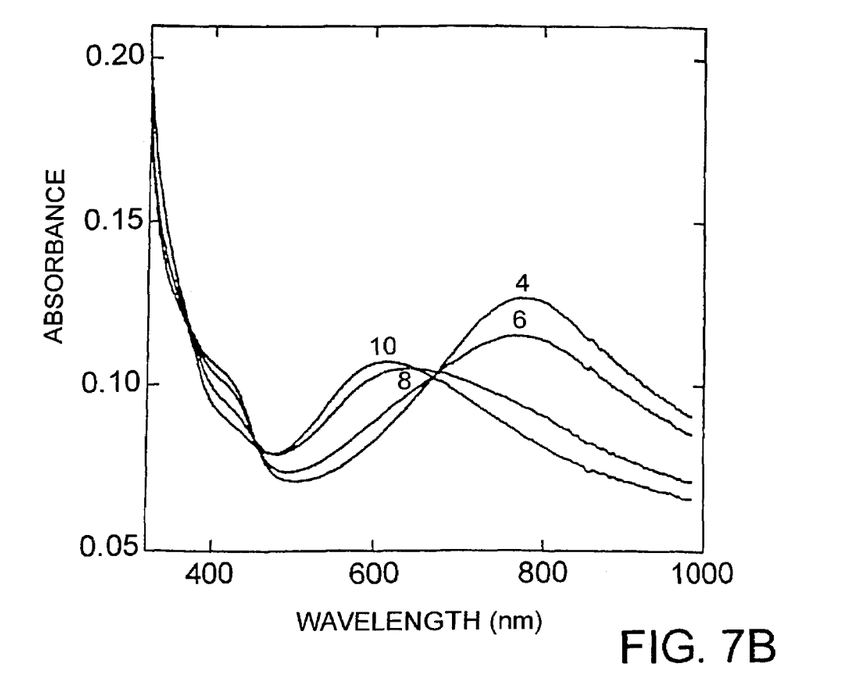
FIG. 7b is a graph showing the visible absorbance and redox behavior of a 50 bilayer film of SPS/polyaniline (prepared at pH 4.0) with decreasing pH values.

FIGS. 7a and 7b show the visible absorption spectra of a film of fifty bilayers wherein PDAC layers alternate with SPS/PA layers, under various pH conditions. As shown in the figures, the multilayer film exhibited similar redox behavior as was observed previously with the solution absorption spectra. This result confirmed that facile electrostatic deposition was feasible with the SPS/PA polymer complex and that the electrical activity was maintained after deposition. In addition, multilayer and bulk films were prepared on indium tin oxide (ITO) slides and four-point probe conductivity measurements were taken. The results showed polymer-complex conductivities in the range of $10^{-3}$ to $10^2$ S/cm.

Example 2

Preparation of Polyphenol-Sulfonated Polystyrene Complex

Horseradish peroxidase (HRP)(enzyme classification number (EC) 1.11.1.7), phosphate and Tris-HCl buffers were obtained from Sigma Chemicals Company, St. Louis, Mo. Phenol, sulfonated polystyrene (SPS) and hydrogen peroxide (30%) were obtained from Aldrich Chemicals, Inc., Milwaukee, Wis. All the chemicals were used as received.

Figure 8A:
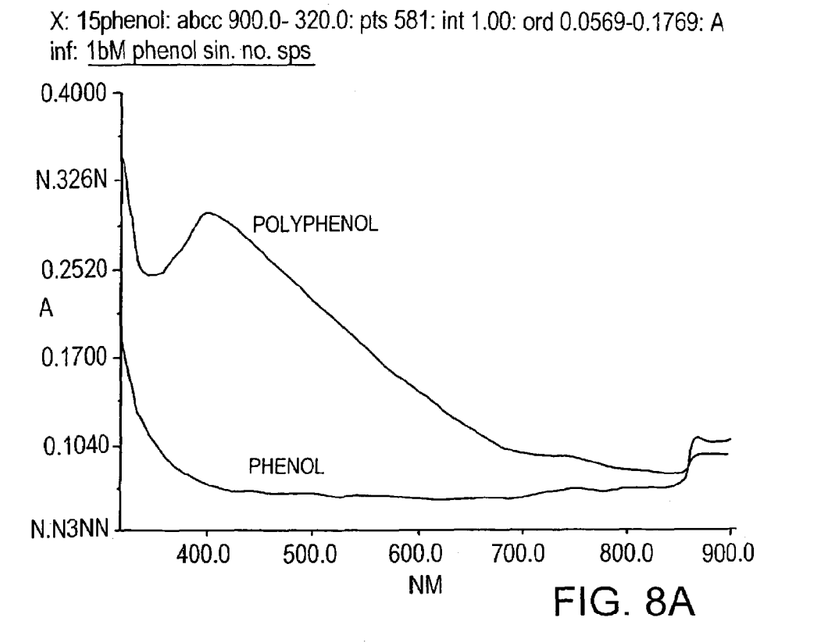
FIG. 8a is a graph showing the visible absorbance of polyphenol without SPS versus phenol monomer. Polyphenol precipitated out of solution as a result of polymerization.
Figure 8B:
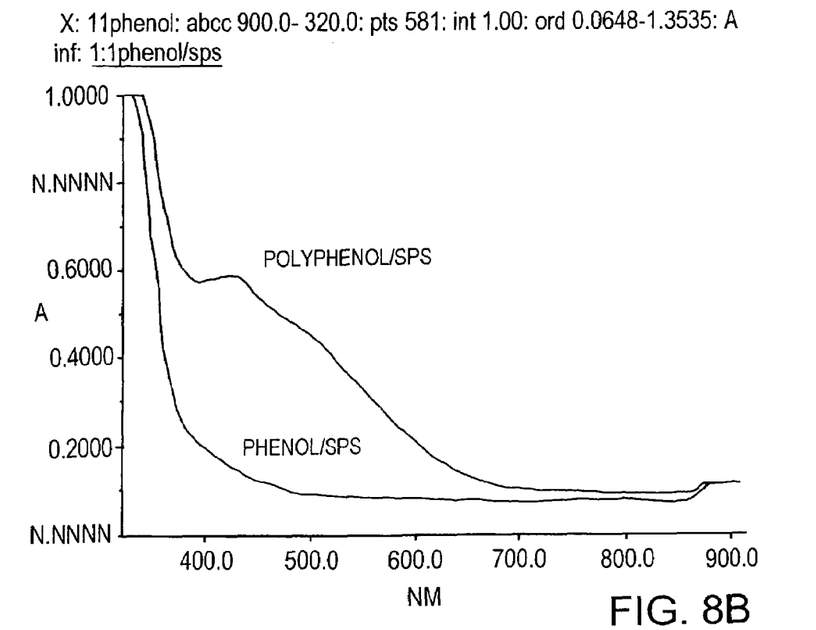
FIG. 8b is a graph showing the visible absorbance of a polyphenol/SPS template versus phenol monomer, where polyphenol did not precipitate out of solution.

The monomer, phenol, was polymerized in a similar fashion as described in Example 1, with sulfonated polystyrene (SPS) in a 1:1 ratio. The progress of this reaction was monitored by the change in visible absorbance. Perkin-Elmer Lambda 9® UV-Vis-near IR spectrophotometer was used for the spectral characterization of the polymer. FIG. 8a is a graph showing the visible absorption of polyphenol without SPS, versus phenol monomer. As shown, there was a significant absorption maximum in the visible spectrum upon polymerization, which indicates formation of polyphenol. However, with time the polymer began to precipitate out of solution. FIG. 8b shows the visible absorption of polyphenol with SPS, versus phenol monomer. As shown again, there was a significant absorption maximum of the polymerized system in the visible spectrum. In this case, there was no observed precipitation of the polymer complex out of solution.

Molecular weight determination was carried out by column chromatography using Protein PAK 300 SW® columns manufactured by Waters Association. Molecular weight as large as 136 kD was measured, indicating polymerization of the phenol and complexation to the SPS template.

Example 3

Preparation of Polyphenol-Lignin Sulfonate Complex

Lignin sulfonate (Lignosol SFX-65, "LGS") was purchased from Lignotech USA (Rothschild, Wis.). The sources of other starting materials have been stated above.

LGS was used as the template for the polymerization of aniline. 5.2 mg of LGS was dissolved in 10 ml of sodium monophosphate buffer (0.1 M) at pH 4.0. 180 µl of aniline was added to this buffer solution (final concentration=195 mM). 2 mg of horseradish peroxidase ("HRP") was then added. 50 µl of hydrogen peroxide (0.025% solution) was added every 10 minutes, with constant stirring, until a total of 200 µl of hydrogen peroxide was added. The reaction was maintained at room temperature and was terminated after 12 hours. The solution was dialyzed using "spectra-pore" membrane bags ($M_w$ cut-off=1 kD) for 72 hours.

Figure 9:
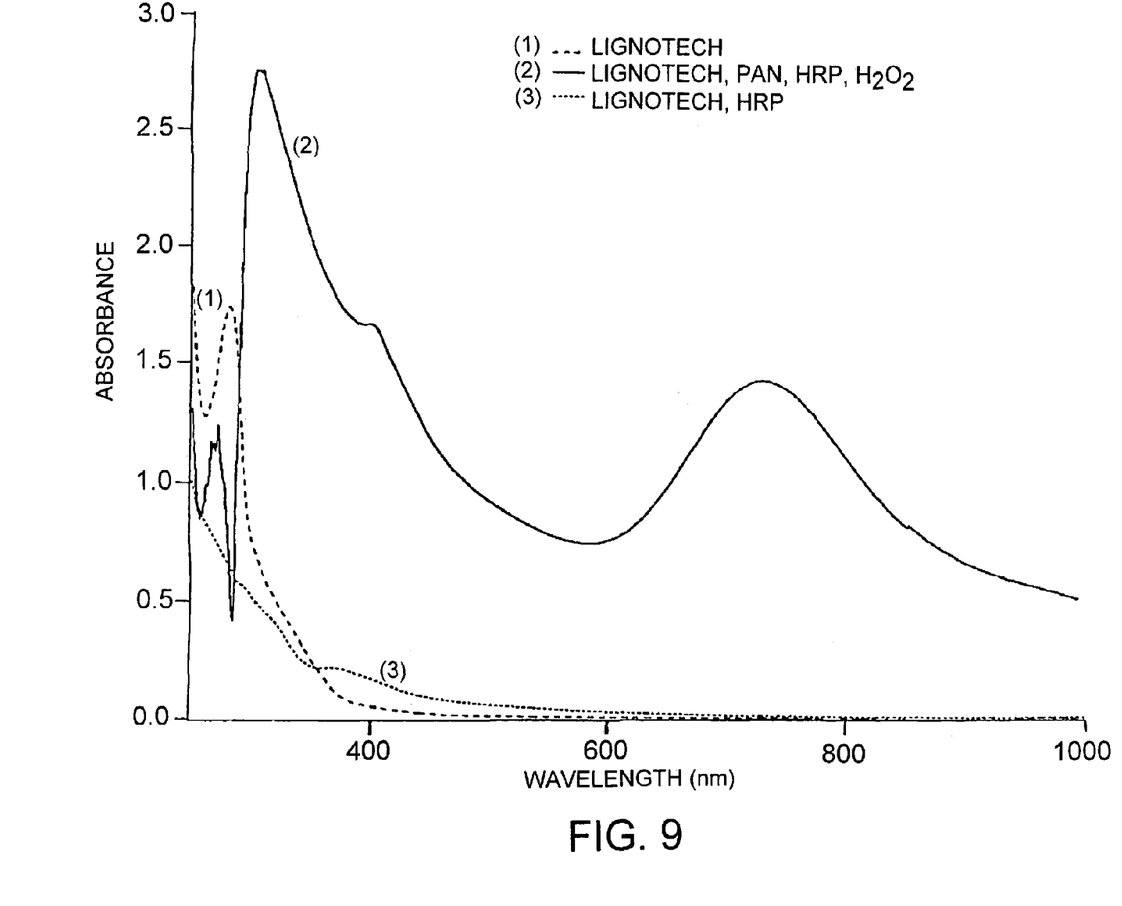
FIG. 9 is a graph showing overlapping visible spectra of (1) lignin sulfonate (Lignotech, "LGS"); (2) polyaniline-LGS, horseradish peroxidase ("HRP"), and hydrogen peroxide; and (3) LGS and HRP.

FIG. 9 is a graph showing overlapping visible absorption spectra of (1) LGS (indicated by - - - ); (2) polyaniline-LGS, HRP, and hydrogen peroxide (indicated by -); and (3) LGS and HRP (indicated by . . . ). Note that spectrum (2) significantly differs from spectra (1) and (3). The intense absorption peaks (at around 300 nm and 750 nm) as shown in spectrum (2) indicate the presence of the conducting or emeraldine salt form of polyaniline.

Example 4

Preparation of Polyaniline-Dodecyl Benzene Sulfonic Acid Micelle Complex

Dodecyl benzene sulfonate (DBSA) was purchased from Aldrich (Milwaukee, Wis.). The sources of other starting materials have been stated above.

Aniline (final concentration=3 mM) and DBSA (final concentration=10 mM) were dissolved in 10 ml of a sodium monophosphate buffer solution (0.1 M, pH 7.0) with horseradish peroxidase (HRP) (total concentration was 0.1-0.15 mg/ml). 100 µl of hydrogen peroxide (0.03%) were added to the solution.

The final products were dialyzed using centricon concentrators (10,000 cut off, Amicon Inc., Beverly, Mass.), dried under vacuum at 50° C., and dissolved in water for further analysis.

Figure 10:
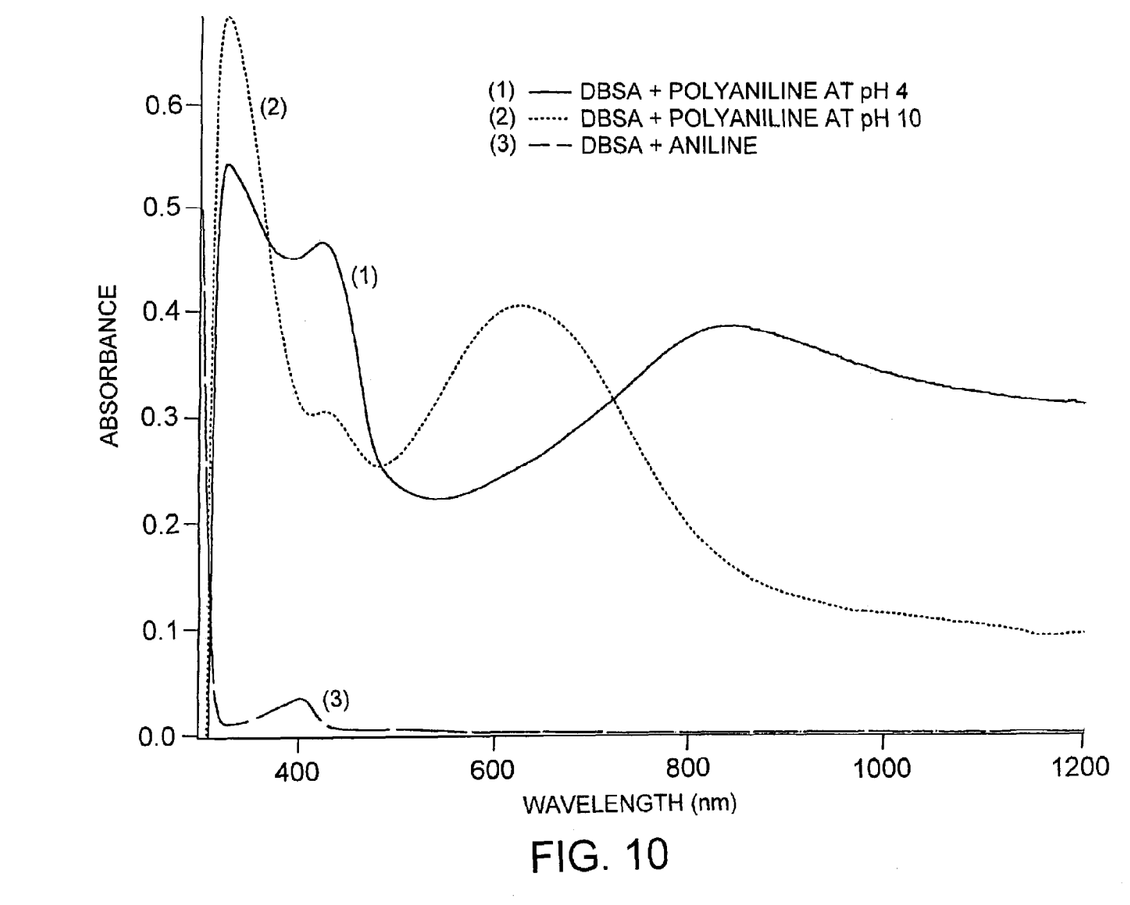
FIG. 10 is a graph showing overlapping visible spectra of (1) polyaniline-dodecyl benzene sulfonic acid ("DBSA") micelle at pH 4; (2) polyaniline-DBSA micelle prepared at pH 4 and adjusted to pH 10; and (3) aniline monomer and DBSA micelle.

FIG. 10 is a graph showing overlapping visible absorption spectra of (1) polyaniline-dodecyl benzene sulfonic acid (DBSA) micelle prepared at pH 4.0, (indicated by -); (2) polyaniline-DBSA micelle prepared at pH 4.0 and adjusted to pH 10.0 (indicated by - - - ); and (3) DBSA micelle and aniline (indicated by - - - ). Note that the spectrum of reaction mixture (1) differs significantly from that of reaction mixture (3) (i.e., the control), showing a strong and broad absorption above 800 nm which indicates the presence of the conducting form of polyaniline. After polymerizing at pH 4.0 (see spectrum (1)), the pH of reaction mixture was adjusted to pH 10.0 (see spectrum (2)), the absorption peaks shifted to 600 nm which indicates the polymer became less conductive. The results reflect the pH dependence of the complex.

Example 5

Preparation of Polyphenol-Dodecyl Benzene Sulfonic Acid Micelle Complex 67 mg of phenol (71.3 mM) and HRP (total concentration =0.1-0.15 mg/ml) were dissolved in 10 ml of a sodium monophosphate buffer solution (0.1M, pH 7.0) in the presence of equimolar DBSA (i.e., 71.3 mM) at room temperature. A total volume of 0.024 ml of hydrogen peroxide (71.3 mM) was added to the solution (about 10 mM added every 5 minutes). The final product (yield was 93.9%, by weight) was dialized using centricon concentrators (10,000 cut off, Amicon Inc., Beverly, Mass.), dried under vacuum at 50° C., and then dissolved in DMSO/water (50/50) solution for further analysis. The molecular weight of the product was determined to be $3.5 \times 10^6$ g/mol. A control experiment was conducted by using denatured enzyme. HRP was denatured by boiling in a 0.1 M sodium monophosphate buffer (pH 7.0) for 30 minutes. The boiled HRP was tested using purpurogallin, and was found to be inactive. No polymerization was observed with the control experiment.

Figure 11:
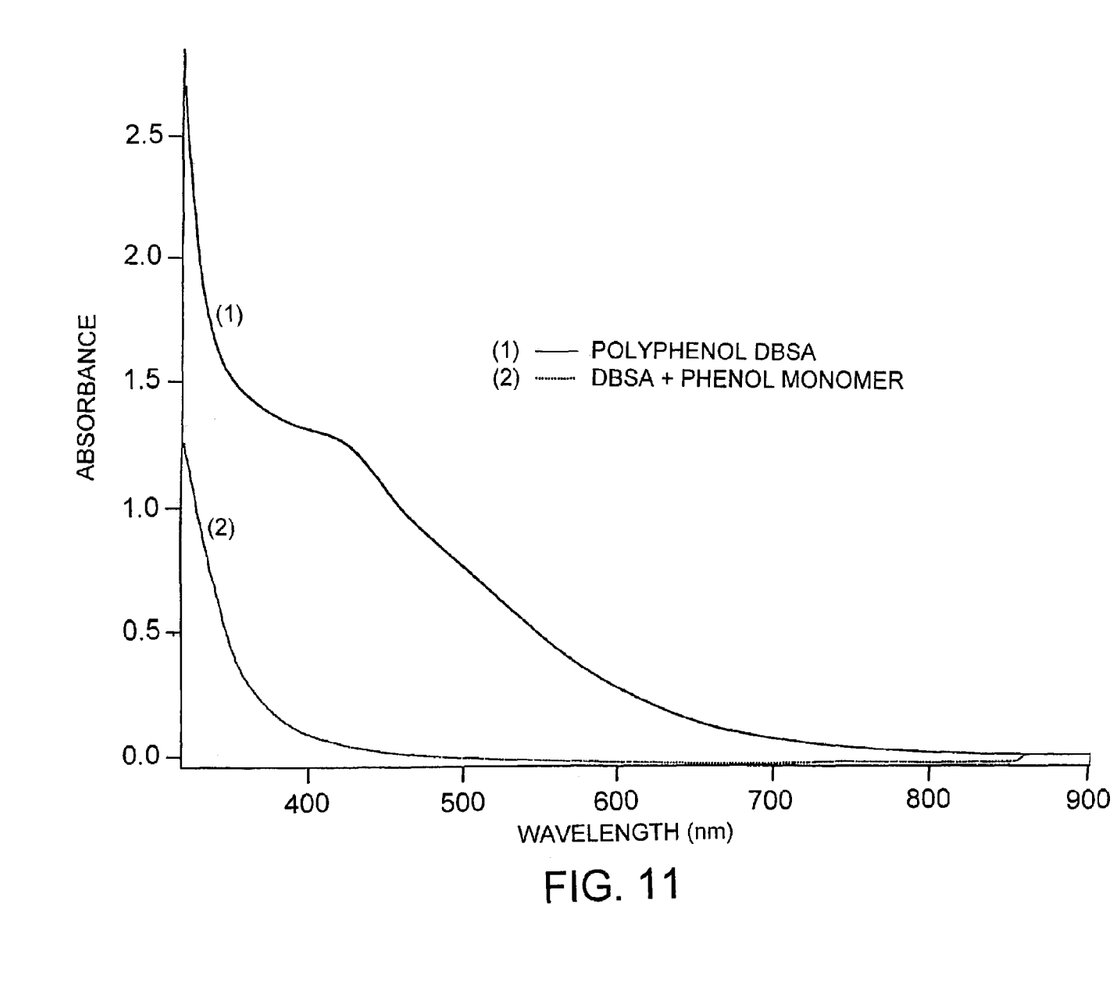
FIG. 11 is a graph showing overlapping visible spectra of (1) polyphenol-DBSA micelle; and (2) phenol monomer and DBSA micelle.

FIG. 11 is a graph showing overlapping visible spectra of (1) polyphenol-DBSA micelle (indicated by -); and (2) phenol monomer and DBSA micelle (indicated by - - - ). Note that spectrum (1) differs significantly from spectrum (2), showing a strong broad absorption above 600 nm and reaching pass 900 nm. This result indicates the presence of the polyphenol complex in the first reaction mixture.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, water-soluble polymers formed by the novel polymerization method can be precipitated from solution by adjusting the pH with a suitable acid or base.

What is claimed is:

1. A polymer-micelle complex comprising:
a polymer bound to a micelle template, wherein the micelle template comprises multiple dodecyl benzene sulfonic acids, the polymer-micelle complex being prepared by a method comprising forming a mixture having a pH of 4 to 10 and containing aniline or phenol, the micelle template and horseradish peroxidase adding hydrogen peroxide to the mixture, and incubating the mixture for a time and under conditions sufficient for the horseradish peroxidase to oxidize the aniline or phenol to form free-radical containing aniline or phenol that aliens around the micelle surface and polymerizes to form the polymer-micelle complex.

* * * * *